United States Patent [19]

Ide et al.

[11] 4,146,033
[45] Mar. 27, 1979

[54] MEDICAL CATHETER

[75] Inventors: Hiroyuki Ide, Fukuoka; Hiroharu Kakiuchi, Tosu; Hirotsune Igimi, Fukuoka; Yoshiomi Saito, Kamakura; Masahiro Shimizu, Yokohama, all of Japan

[73] Assignees: Hisamitsu Pharmaceutical Co., Inc., Saga; Nippon Zeon Co., Ltd., Tokyo, both of Japan

[21] Appl. No.: 845,235

[22] Filed: Oct. 25, 1977

Related U.S. Application Data

[63] Continuation of Ser. No. 668,209, Mar. 18, 1976, abandoned.

[51] Int. Cl.² ............................................. A61M 25/00
[52] U.S. Cl. .................................. 128/348; 128/349 R; 128/350 R
[58] Field of Search ........................ 260/2 A; 428/36; 128/349 R, 348, 350 R; 526/11.2

[56] References Cited

U.S. PATENT DOCUMENTS

| 3,457,197 | 7/1969 | Hsieh et al. ............................... 260/2 |
| 3,633,578 | 1/1972 | Roth et al. ............................ 128/214 |
| 3,663,288 | 5/1972 | Miller ..................................... 117/7 |
| 3,695,921 | 10/1972 | Shepherd et al. ....................... 117/72 |
| 3,708,461 | 1/1973 | Karastu et al. ........................ 260/79 |
| 3,759,788 | 9/1973 | Gajewski et al. ..................... 195/1.8 |
| 3,790,524 | 2/1974 | Saito et al. ....................... 260/45.8 N |
| 3,822,241 | 7/1974 | Hani et al. ............................. 260/79 |

OTHER PUBLICATIONS

Raible et al., "Elastomers for Use in Heart Valves", Rubber Chemistry and Technology 39, (4), 1276-1287 (1966).

Primary Examiner—Harold D. Anderson
Assistant Examiner—E. A. Nielsen
Attorney, Agent, or Firm—Browdy and Neimark

[57] ABSTRACT

A novel medical catheter, formed of a rubber component comprising substantially a homopolymer of epichlorohydrin and fillers comprising silica and/or silicates, possesses sufficient tensile strength and flexibility and meets the sanitary requirements.

4 Claims, 1 Drawing Figure

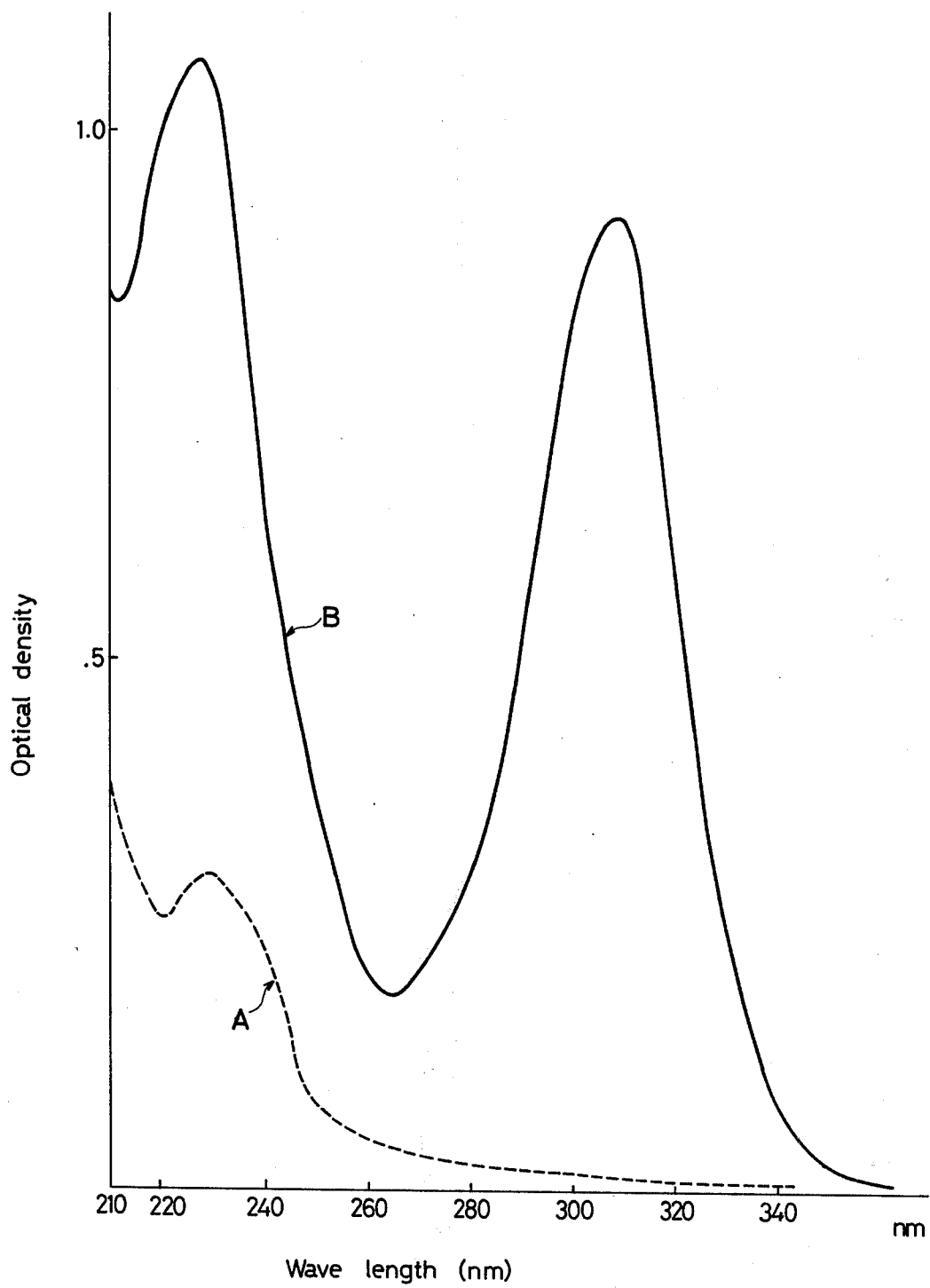

MEDICAL CATHETER

This is a continuation of application Ser. No. 668,209 filed Mar. 18, 1976, now abandoned.

BACKGROUND

Medical catheters are formed of biocompatible material, and are constructed of a size and shape so they may be introduced into the human body without causing excessive trauma, their function being to transmit a liquid to or from a body cavity or organ.

Conventional medical catheters are roughly divided into two groups; metal catheters of high rigidity and rubber catheters of flexibility. Since both catheters have advantages and disadvantages for medical use, it is said that there is no catheter meeting fully the various delicate requirements of eliminating retained fluids from body cavities and organs, introducing medicinal solutions into the cavities and organs, eliminating the contents from gastro-intestinal, esophageal and tracheal tracts, or introducing some substances into the tracts.

The most important thing in the medical use of catheters is to avoid bacterial infections, and for this purpose, either boiling-sterilization (100° C.) or steam-sterilization in an autoclave (121° C.) is usually carried out before using catheters. Consequently, heat-stability at temperatures of, at least, 100°–130° C. is required for the catheter. Since catheters are inserted into the living body, their hardness should not be so high as to cause stimulation to the tissues which is subsequently followed by inflammation. But some degree of hardness is required for enabling the fluids or liquids to pass smoothly when some retained body fluids are eliminated from the body or when some medicinal solutions are introduced into the body. In addition, chemical resistance to the fluids and medicinal solutions is also required for the catheter.

As described above, miscellaneous specific properties are required for catheters but most of the catheters available are still made from natural rubber. Although the catheter made from natural rubber is excellent in flexibility, it lacks resistance to heat and chemicals. Thus, use of such a catheter has occasionally caused such troubles as swelling and dissolution of the catheter itself by the body fluids and medicinal solutions, extraction of the additives from the catheter by these fluids and solutions, aging of the catheter by sterilization and during storage as well as striking changes in elasticity, flexibility and tensile strength. It is said that this type of catheter is not a perfect catheter for medical use, having the drawbacks as above.

There are various other kinds of catheters, which are made from silicone rubber, butyl rubber, polychloroprene, polyvinyl chloride, polyethylene and polytetrafluoroethylene, in addition to the catheters made from natural rubber. However, there have been found no catheters to satisfy all the requirement including flexibility, hardness, heat-stability, resistance to body fluids and chemicals.

In particular, there have not been found any catheters suitable for introducing the gallstone solubilizer, which have been developed by the present inventors, directly into the biliary system.

SUMMARY

The inventors have made an attempt to improve catheters which have many kinds of drawbacks as stated above, and succeeded in developing the novel medical catheter of the present invention, which possesses suitable flexibility, hardness, heat-stability and offers chemical resistance to the body fluids and medicinal solutions.

DESCRIPTION OF THE DRAWING

FIG. 1 shows ultra-violet spectra of the extractive substances both from the catheter of the present invention (A) and a catheter made from natural rubber (B).

DETAILED DESCRIPTION

The present invention relates to a catheter which has the characteristics of sufficient tensile strength and flexibility; and strong resistance to sterilization procedures and chemicals, and which meets fully sanitary requirements. More particularly, the present invention relates to a catheter comprising substantially a homopolymer of epichlorohydrin, which is compounded with anhydrous silica and/or silicates and vulcanized after formation.

An important characteristic of the present invention is that substantial homopolymer of epichlorohydrin is used as the rubber component to prepare a novel catheter. Preparation of the catheter from this substantial homopolymer of epichlorohydrin has led to a reduction in the extractive substances which can be leached from the catheter as well as enhanced resistance to chemicals, especially terpenes without doing any damage to flexibility and hardness. The "substantial homopolymer of epichlorohydrin" stated herein indicates an epichlorohydrin homopolymer including an epichlorohydrin copolymer with 0.5–10 mol% of unsaturated epoxides such as butadiene mono-oxide, allylglycidylether, glycidylacrylate and glycidylmethacrylate, which enables vulcanization with sulfur or a peroxide. Generally speaking, the vulcanizates of epichlorohydrin rubbers are excellent materials which possess sufficient tensile strength, flexibility, heat-stability and strong resistance to chemicals. To meet the sanitary requirements for medical use, preferred epichlorohydrin rubber comprises substantially a homopolymer of epichlorohydrin. For example, in the test of the rate of potassium permanganate ($KMnO_4$) consumption to water soluble extracts from polymers which is regulated in the standard promulgated by the Ministry of Health and Welfare of Japan, the homopolymer of epichlorohydrin gave far better results as compared to that of the equimolar copolymer of epichlorohydrin. This comes from the great difference between both polymers in their resistance to water.

The substantial homopolymer of epichlorohydrin of the present invention may be prepared easily by solution polymerization or bulk polymerization of epichlorohydrin using an organic aluminum compound as a main catalyst. In the present invention, fillers are compounded to said polymer, a mixture of which is further vulcanized. To obtain a vulcanizate of satisfactory tensile strength, the viscosity of said polymer should be more than 30 in Mooney viscosity ML 1 + 4(100° C.). In addition to said polymer there is added a small amount of conventional antioxidants such as amines, phenols and dithiocarbamates usually at the time of manufacture or, in certain circumstances, at the time of vulcanization. But it is preferred that as little antioxidants as possible be compounded in said polymer. Since said polymer used in the present invention is prepared by solution and bulk polymerization, it does not contain any emulsifiers which may usually be detected in the products prepared by emulsion polymerization. Lack of emulsifier in the catheter of the present invention is advantageous for sanitary reasons. In the present invention, said catheter of excellent properties may be obtained by using only a substantial homopolymer of epichlorohydrin as a rubber component. Fillers include such conventional fillers as carbon, calcium carbonate and magnesium carbonate, and vulcanizers include such conventional vulcanizers as sulfur, polysulfide and thiourea.

Another important characteristic of the present invention is to compound silica and/or silicates as well as conventional fillers in said substantial homopolymer of epichlorohydrin. By this combination of fillers, the inventors succeeded in preparing the desired product which offers strong resistance to chemicals and possesses sufficient flexibility and hardness. In addition little or no extractive substances may be yielded from said catheters. That is to say, the inventors succeeded in offering said catheter which may satisfy the "Requirement of Rubber Tube on Disposable Transfusion and Infusion assemblies" (Notification of Ministry of Health and Welfare of Japan No. 301, issued on Aug. 10, 1970) and pass the standard of "Injectionsflaschen, Stopfen (Rubber closure for injection vial)" Deutsche Normen, DIN 58366) and the standard specified in the "General Test, Plastic Containers for Aqueous Infusions" of the Japanese Pharmacopoeia VIII. The catheter of the present invention may be useful for making various types of catheters, for example, bag catheters, Bozeman-Fritsch catheters, de Pezzer catheters, elbowed catheters, eustachian catheters, lobster-tail catheters, Nelaton's catheters, Phillip's catheters, prostatic catheters, rat-tail catheters, Schroetter's catheters, sigmoid catheters, Skene's catheters, tracheal catheters, two way catheters, vertebrated catheters, whistle-tip catheters and winged catheters.

The catheter of the present invention may be prepared as follows: To said substantial homopolymer of epichlorohydrin is added silca and/or silicate as fillers, further added vulcanizers and adequately mixed. This mixture is made into a thin tube of small diameter, and subsequently, vulcanized by heating.

Although conventional fillers such as carbon and calcium carbonate are available, use of silica and/or silicates may afford a suitable hardness, as well as little or no water-soluble extractives from the catheter. Silica and silicates include finely pulverized silica, hydrous silica, anhydrous silica, and natural and synthetic silicates, for example, hydrous magnesium silicate, hydrous aluminum silicate, and hydrous calcium silicate. Of these silicates, well-used aluminum silicate and magnesium silicate are less effective in the reinforcement of said polymer, but on the contrary, more effective in the flow behavior at the time of extrusion and in providing gloss on the surface of the vulcanized tube, than finely pulverized silica. Combined use of silica and silicates with said polymer gives the tube a smooth surface as well as excellent tensile strength. These fillers may cause an increase in the viscosity of unvulcanized rubber as well as in the hardness and modulus of vulcanized rubber. However, compounding too large quantity of these fillers causes such an increased hardness that the tube become stiff and attains large tension set, and also causes an increased residue on evaporation in the test of extractive substances, so that the tube may not be things of practically no use. These fillers compounded in the tube afford less residue on evaporation in the above test than do other fillers, but it is preferred that as little fillers as possible are compounded in the tube in terms of the test of extractive substances. On the other hand, to support a sufficient tensile strength, some definite amount of these fillers must be compounded in said polymer. For the purpose of adjusting the balance between high tensile strength and little residue on evaportion, the fillers consisting of silica or silicates of the present invention, are compounded as follows: 10–170, preferably 20–130 parts by weight are mixed with 100 parts by weight of said substantial homopolymer of epichlorohydrin.

In the preparation of the catheter of the present invention, the following conventional vulcanizing agents are all available for valcanization of the molded tubes; sulfur, sulfur compounds, guanidines, aldehyde-ammonia compounds, thiazoles, imidazolines, thioureas, thirams, dithiocarbamates, xanthates, metal oxides, amines, fatty acids, peroxides and their derivatives. Combination of, at least one compound selected from metal oxides such as magnesium oxide, barium oxide, calcium oxide and zinc oxide, at least one compound selected from 2-mercaptoimidazolines, 2-mercaptopyrimidines and thioureas, and at least one compound selected from sulfur, an organic polysulfide dicumyl peroxide and di-tert-butyl peroxide gives the most favorable results. Preferable amounts of each of the combined vulcanizing agents are as follows: 0.4 to 9.0, preferably 2.0 to 3.5 parts by weight of metal oxides, 0.2 to 2.0, preferably 0.5 to 1.5 parts by weight of 2-mercaptopyrimidines or thioureas and 0.1 to 2.5, preferably 0.2 to 0.8 parts by weight of sulfur or organic polysulfide. These combinations cause an increased rate of vulcanization and a decreased extractive substances, and prevent coloration of the valcanizate. The catheter of the present invention gains advantages over the conventional catheters as described in the following:

1. Said catheter is not stiff as compared to a catheter made from resins. And said catheter has a sufficient tensile strength and tear resistance as compared to a catheter made from rubbers.

2. Said catheter is strikingly resistant to heat-aging. Accordingly, it does not cause such unexpected changes in the physical and physicochemical properties in the course of long-term storage as natural rubber catheters do.

3. Said catheter offers a strong resistance to vegetable oils such as olive oil, lemon oil, caraway oil, bergamot oil and castor oil, and to terpenes containing aliphatic and alicyclic hydrocarbons, especially to d-limonene.

4. Said catheter demonstrates low toxicity, namely, no death of animals in the acute systemic toxicity test and no hemolysis in the hemolysis test. Said catheter meets fully the requirement of pyrogen and intracutaneous reactivity test. In addition, in the chemical tests for heavy metals, potassium permanganate-reducing substances, residue on evaporation and ammonium none was detected. From this, said catheter appears to be completely safe for biological use.

Some examples of the process for manufacturing the catheter of the present invention as well as the testing methods and results of said catheter are illustrated in the following.

Example of the process for manufacturing catheter

The epichlorohydrin rubber compound was prepared by mixing the ingredients shown in Table 1 on a mill.

Table 1

| | Parts by weight |
|---|---|
| Epichlorohydrin rubber(Hydrin 100)* | 100 |
| Stearic acid | 1.0 |
| Anhydrated silica, light | 12 |
| Aluminum silicate, natural | 50 |
| Magnesium silicate | 38 |
| Titanium oxide | 3.0 |
| Magnesium oxide | 3.0 |
| 2-Mercaptoimidazoline | 0.8 |
| Sulfur | 0.8 |

*Manufactured by B.F. Goodrich Chemical Co., Inc.

The rubber compound was made into thin tubes by extrusion. The tubes were wound a round a stainless-steel cylinder of approximately 200 mm in diameter and vulcanized at 165° C. for 1.5 hours. The vulcanized tubes were cut in lengths of 5 meters each, having outside diameter of 4.8 mm, inside diameter of 2.8 mm and cross-sectional area of 47.7 $mm^2$.

Example of testing (1)

The catheter manufactured according to the above Example was examined for their physical and physico-chemical properties, that is, tensile strength, elongation, hardness, tear resistance as well as resistance to heat-aging, boiling water, steam under pressure, warm water and chemicals, comparing with that of conventional catheters and tubes made from natural and other synthetic polymers.

Table 2

| No. of specimen | Tube materials | Inside diameter (mm) | Outside diameter (mm) | Cross-sectional area ($mm^2$) |
|---|---|---|---|---|
| 1* | Epichlorohydrin rubber | 2.80 | 4.80 | 47.7 |
| 2** | Natural rubber | 3.00 | 4.50 | 35.3 |
| 3** | silicone rubber | 4.15 | 6.15 | 64.6 |
| 4** | Teflon (polytetrafluoroethylene) | 3.95 | 4.95 | 27.9 |
| 5** | Polyethylene | 4.15 | 6.70 | 86.9 |

*Catheter of the present invention
**Reference catheter

A. Tensile test (tensile strength, elongation), hardness and tear resistance (Tensile test)

Tensile strength was measured in a Schoppers's type tensile tester at a tensile rate of 500 mm per minute, holding the initial distance of 50 mm between two jaws of clamps. The tensile strength obtained was divided by the cross-sectional area of test specimen to convert into the unit of Kg/$cm^2$. Elongation was obtained on the basis of change in the distance between two bench marks (20 mm). Results were obtained from the mean by weight of measurement of 4 specimens.

(Hardness)

Hardness of the surface of test specimens was measured by Wallace micro hardness tester. Measurement was carried out on 2 points of the surface and averaged. Readings in hardness degree given by this hardness tester are approximately equal to the readings in the Shore A hardness degree which is scaled by International Rubber Hardness Degree (IRHD) (ASTM D-1415-56T).

(Tear resistance)

In extrusion products such as rubber tube, tear resistance in the direction of extrusion (axial direction) is markedly different from that in the rectangular direction to the axis. Therefore, measurement of tear resistance in both direction was carried out, using Schopper's type tensile tester at a travel rate of 500 mm per minute.

For measurement of tear resistance in the axial direction, previous tearing in this direction was made on the test specimen, both terminal ends of which were clamped with jaws of the tensile tester. For measurement of tear resistance in the rectangular direction to the axis, a single nick of 2 mm in length was cut in this direction and both terminal ends of the tube specimen were attached to the tensile tester.

The results were obtained from the mean value by weight of measurement of 4 specimens according to the Japanese Industrial Standards, JIS K-6301, and shown in Table 3.

Table 3

| No. of specimen | Tensile strength (Kg/$cm^2$) | Elongation (%) | Hardness | Tear resistance (Kg/cm) Axial | Tear resistance (Kg/cm) Rectangular to axis |
|---|---|---|---|---|---|
| 1 | 21.1 | 390 | 74.0 | 17.5 | 5.3 |
| 2 | 43.9 | 470 | 62.2 | 22.5 | 1.3 |
| 3 | 17.2 | 360 | 46.1 | 10.5 | 2.5 |
| 4 | 63.3 | 180 | 99.1 | — | — |
| 5 | 22.2 | 430 | 97.9 | — | — |

As shown in Table 3, Teflon (Specimen No. 4) and polyethylene (Specimen No. 5) were too stiff (hardness test), but in contrast silicone rubber (Specimen No. 3) was low in strength on the whole. Tear resistance of natural rubber (Specimen No. 2) exhibited a striking difference depending on the direction of tear. Strength of the tube specimen of the present invention was well-balanced, which suggested that it was a rubber-like material.

B. Heat-aging

Each specimen was heat-aged at 120° C. for 24 hours by the oven method. Tensile strength, elongation and hardness of the aged specimens were measured by the methods described previously, and the change ratios were calculated on the basis of the values before heat-aging. The results were shown in Table 4.

Table 4

| | Resistance to heat-aging | | | | | |
|---|---|---|---|---|---|---|
| No. of specimen | Tensile strength (Kg/$cm^2$) | Change ratio (%) | Elongation (%) | Change ratio (%) | Hardness | Change ratio (%) |
| 1 | 20.2 | (−4.3) | 250 | (−35.9) | 76.5 | (+2.5) |
| 2 | 4.5 | (−89.8) | 70 | (−85.1) | 45.1 | (−17.1) |
| 3 | 16.1 | (−6.4) | 330 | (−8.3) | 53.6 | (+7.5) |
| 4 | 62.1 | (−1.9) | 170 | (−5.6) | 98.9 | (−0.2) |

Table 4-continued

| | | Resistance to heat-aging | | | | |
|---|---|---|---|---|---|---|
| No. of specimen | Tensile strength (Kg/cm$^2$) | Change ratio (%) | Elongation (%) | Change ratio (%) | Hardness | Change ratio (%) |
| 5* | Non-measurable | | | | | |

*The specimen was too softened to measure

These results indicate that polyethylene is of no use at high temperature and natural rubber become practically of no use when it is exposed to the circumstance of high temperature in the course of long-term storage.

C. Resistance to water and chemicals

The tests for resistance to steam under pressure, boiling water and chemicals were carried out according to JIS K-6301, but the shape of test specimens and the condition of treatment were as follows.

(1) Test specimen

Length of the tube tested was approximately 100 mm for measurement of tensile strength and approximately 20 mm for measurement of the volume change.

(2) Condition of treatment

Resistance to steam:

Test specimens were exposed to steam in an autoclave maintained at a temperature of 121° C. and a pressure of 1 Kg/cm$^2$ for 30 minutes.

Resistance to boiling water:

Test specimens were placed in a boiling water (100° C.) for 60 minutes.

Resistance to chemicals:

Test specimens were immersed in chemicals kept at temperatures of 37°±1° C. for 7 days. The results are shown in Table 5 to 8.

Table 5

| | | Resistance to steam under pressure | | | | |
|---|---|---|---|---|---|---|
| No. of specimen | Tensile strength (Kg/cm$^2$) | Change ratio (%) | Elongation (%) | Change ratio (%) | Hardness | Change ratio (%) |
| 1 | 12.9 | (−38.8) | 480 | (+23.0) | 74.0 | (±0) |
| 2 | 18.4 | (−58.1) | 300 | (−36.0) | 65.5 | (+5.3) |
| 3 | 15.5 | (−9.9) | 360 | (±0) | 49.1 | (+6.5) |
| 4 | 60.0 | (−5.2) | 130 | (−27.8) | 98.7 | (−0.4) |
| 5 | 40.4 | (+82.1) | 420 | (−2.3) | 98.6) | (+0.7) |

Table 6

| | | Resistance to boiling water | | | | |
|---|---|---|---|---|---|---|
| No. of specimen | Tensile strength (Kg/cm$^2$) | Change ratio (%) | Elongation (%) | Change ratio (%) | Hardness | Change ratio (%) |
| 1 | 11.7 | (−44.5) | 450 | (+15.4) | 74.0 | (±0) |
| 2 | 17.9 | (−59.2) | 300 | (−36.2) | 65.5 | (+5.3) |
| 3 | 14.2 | (−11.8) | 340 | (−5.6) | 49.1 | (+6.5) |
| 4 | 54.2 | (−13.9) | 110 | (−38.0) | 98.7 | (−0.4) |
| 5 | 21.9 | (−1.4) | 450 | (+4.7) | 97.8 | (−0.4) |

The results shown in Table 5 and 6 indicates that the catheter of the present invention may offer sufficient resistance to steam and boiling sterilization.

Table 7

| | | Resistance to olive oil | | | | | |
|---|---|---|---|---|---|---|---|
| No. of specimen | Tensile strength (Kg/cm$^2$) | Change ratio (%) | Elongation (%) | Change ratio (%) | Hardness | Change ratio (%) | Volume change (%) |
| 1 | 16.0 | (−24.2) | 400 | (+2.6) | 75.0 | (+1.4) | 3.7 |
| 2 | 9.8 | (−77.6) | 270 | (−42.6) | 48.3 | (−22.3) | 89.8 |
| 3 | 10.5 | (−38.9) | 270 | (−25.0) | 45.8 | (−0.7) | 2.0 |

The results of testing for resistance to olive oil indicate that natural rubber as well as silicone rubber are useless for the vegetable oils, but on the contrary, the catheter of the present invention offered strong resistance to the oils.

Table 8

| | | Resistance to d-limonene | | | | | |
|---|---|---|---|---|---|---|---|
| No. of specimen | Tensile strength (Kg/cm$^2$) | Change ratio (%) | Elongation (%) | Change ratio (%) | Hardness | Change ratio (%) | Volume change (%) |
| 1 | 6.5 | (−69.2) | 510 | (+30.8) | 45.3 | (−38.8) | 31.7 |
| 2 | 1.4 | (−96.7) | 80 | (−83.0) | 29.1 | (−53.3) | 295.7 |
| 3 | 0.3 | (−98.3) | 10 | (−97.3) | 26.5 | (−42.5) | 232.7 |

D. Chemical and biological tests

Chemical test:
1. Heavy metals
2. Potassium permanganate (KMnO$_4$)-reducing substances
3. Residue on evaporation
4. Ammonium 5. Ultra-violet absorption spectrum
Biological tests:
6. Acute systemic toxicity test
7. Hemolysis test
8. Pyrogen test
9. Intracutaneous reactivity test
10. Implantation test The above tests were carried out according to the German standard (Deutsche Normen, DIN 58366) and the Japanese pharmacopoeia 8th Edition, "General tests, Plastic Container for Aqueous Infusions". The test results were shown in Table 9-1.

made from natural rubber (Specimen No. 2) and silicone rubber(Specimen No. 3) are not available Example of testing (2)

Comparison of commercially available epichlorohydrin homopolymers with epichlorohydrin-ethylene oxide compolymers was made on the water-resistance. These epichlorohydrin polymers illustrated in Table 10 were used for the above chemical tests. Compounding the polymers with fillers was carried out according to the Table 1 in the Example of "the process for manufacturing the catheter", and the resulting polymer com- Table 9-1

| | Chemical test by Extractive Substances | | | | | | | |
|---|---|---|---|---|---|---|---|---|
| Test | Catheter of the present invention | DIN 58366 | Interpretation* Standard No. 301** | JP8 | Natural rubber Catheter | DIN 58366 | Interpretation* Standard No. 301** | JP8 |
| Heavy metals | $4.6 \times 10^{-3}$ (mg/10ml) | C | C | C | $9.2 \times 10^{-3}$ (mg/10ml) | R | R | R |
| KMnO$_4$-reducing substances | 0.4 (ml/10ml) | C | C | C | 3.7 (ml/10ml) | C | C | C |
| Residue on evaporation | 0.1 (mg/20ml) | C | C | C | 1.9 (mg/20ml) | R | R | R |
| Ammonium | less color than control solution | C | — | C | more cloir than control solution | R | — | R |
| UV spectrum*** (220nm) | 0.23(O.D.) | — | — | C | scale out | — | — | R |

*C: complied with the standards; R: rejected from the standards.
**The standards notified by the Ministry of Health and Welfare of Japan No. 301
***O.D. : optical density
UV spectra of extractive substances from the catheter of the present invention and from natural rubber catheter are illustrated in the Drawing.

Table 9-I indicates that the catheter of the present invention is strikingly safe as compared to the natural rubber catheter tested.

pounds were made into tubes, and subsequently, vulcanized at 170° C. for 60 minutes.

Table 10

| No. of specimen | Trade name | Polymer species | Manufacturer |
|---|---|---|---|
| 6* | Hydrin 100 | Epichlorohydrin homopolymer | B.F. Goodrich chemicals Co., Inc. |
| 7** | Hydrin 200 | Epichlorohydrin/Ethylene oxide 50/50 mole % copolymer | " |
| 8* | Hercler H | Epichlorohydrin homopolymer | Hercules Co., Inc. |
| 9** | Hercler C | Epichlorohydrin/Ethylene oxide 50/50 mole % copolymer | " |
| 10* | Gechron 1000 | Epichlorohydrin homopolymer | Nippon Zeon Co. Ltd. |
| 11** | Gechron 2000 | Epichlorohydrin/Ethylene oxide 50/50 mole % copolymer | " |

*Polymer of the present invention
**Reference polymer

Each vulcanized tube was cut into 5 mm in length to

Table 9-II

| | Biological Tests | | | | | | | |
|---|---|---|---|---|---|---|---|---|
| Test | Catheter of the present invention | DIN 58366 | Interpretation Standard No. 301 | JP8 | Natural rubber catheter | DIN 58366 | Interpretation Standard No. 301 | JP8 |
| Acute systemic toxicity | No. of death 0/10 | C | C | C | No. of death 1/10 (test solution B) | R | R | R |
| Hemolysis | No hemolysis | C | C | C | Hemolysis observed | R | R | R |
| Pyrogen | No temperature rise | C | C | C | No temperature rise | C | C | C |
| Intracutaneous reactivity | No erythema, edema and hemorrhage | — | — | C | erythema, edema or hemorrhage observed | — | — | R |
| Implantation | No hemorrhage and encapsulation | — | — | C | No hemorrhage and encapsulation | — | — | R |

From these results, it is found that only the catheter or the present invention may offer resistance sufficiently to d-limonene preparation whereas the catheter prepare a test specimen. Eight specimens obtained from each vulcanized tube were immersed in 150 ml of deionized water maintained at 60° C. for 30 minutes. 100 ml of this immersion solution was transferred into an Erlenmeyer flask, to which were added 10 ml of 0.01 N KMnO₄ solution together with 5 ml of 25% sulfuric acid solution. Immediately after boiling of this mixture for 5 minutes, 10 ml of 0.01 N sodium thiosulfate solution was added. The resulting solution was titrated with 0.01 N KMnO₄ solution. The results were shown in Table 11.

Table 11

| No. of specimen | KMnO₄-reducing substances extracted with warm water |
|---|---|
| 6 | 4.20 ppm |
| 7 | 32.00 |
| 8 | 4.36 |
| 9 | 22.90 |
| 10 | 3.44 |
| 11 | 21.70 |

The results indicate that extractive substances from the tubes of the present invention are far less than that from reference tubes.

Judging from the above facts, it is evident that the catheter of the present invention is suitable for medical use. That is to say, the catheter wherein the substantial homopolymer of epichlorohydrin is used as the rubber component has such characteristics as high flexibility and strong resistance to water and chemicals. In addition, the catheter wherein silica and/or silicates are compounded as fillers possesses a sufficient hardness and afford little extractive substances from the catheter itself.

What we claim is:

1. The method of transferring liquids to or from body cavities or organs through a medical catheter formed of epichlorohydrin polymer tubing, said medical catheter also comprising admixed with said epichlorohydrin polymer a filler, and said epichlorohydrin polymer being selected from the group consisting of epichlorohydrin homopolymers and copolymers of epichlorohydrin with 0.5–10 mol percent unsaturated epoxide.

2. A method in accordance with claim 1 comprising using said medical catheter to introduce a medicinal solution into the body.

3. A method in accordance with claim 2 wherein said catheter is used to introduce into the body a liquid for dissolving gall stones.

4. A method in accordance with claim 3 wherein said liquid is d-limonene.

* * * * *